(12) United States Patent
DiMarino et al.

(10) Patent No.: US 6,764,306 B1
(45) Date of Patent: Jul. 20, 2004

(54) SYSTEM AND PROCESS FOR MANAGING DENTAL BURS

(76) Inventors: James C. DiMarino, 140 Rugby Pl., Woodbury, NJ (US) 08096; Susan S. DiMarino, 140 Rugby Pl., Woodbury, NJ (US) 08096

( * ) Notice: Subject to any disclaimer, the term of this patent is extended or adjusted under 35 U.S.C. 154(b) by 0 days.

(21) Appl. No.: 09/338,725

(22) Filed: Jun. 23, 1999

(51) Int. Cl.[7] .............................. A61C 13/38; A61C 3/02

(52) U.S. Cl. ........................ 433/77; 433/165; 206/369

(58) Field of Search .................... 433/77, 165, 166, 433/215; 206/368, 369

(56) References Cited

U.S. PATENT DOCUMENTS

| | | | | |
|---|---|---|---|---|
| 4,011,829 A | * | 3/1977 | Wachsmann | 206/534 |
| 4,253,830 A | * | 3/1981 | Kazen et al. | 433/77 |
| 4,900,252 A | * | 2/1990 | Liefke et al. | 433/27 |
| 5,006,066 A | * | 4/1991 | Rouse | 433/77 |
| 5,078,597 A | * | 1/1992 | Caplin | 433/18 |
| 5,394,983 A | * | 3/1995 | Latulippe et al. | 206/370 |
| 5,890,897 A | * | 4/1999 | Kruger et al. | 433/75 |

* cited by examiner

*Primary Examiner*—John J. Wilson
(74) *Attorney, Agent, or Firm*—Knoble Yoshida & Dunleavy, LLC

(57) ABSTRACT

A system and method for managing dental burs includes a carrier that is customized to hold a selection of burs that a particular dentist prefers for a given procedure. Accordingly, each dentist will have a separately identifiable carrier for such procedures as amalgam and composite fillings, veneer, crown and bridge preparation, post and core procedures, endodontics, emergency treatments and other procedures, such as those that are attendant to removable prosthodontics. In addition, the carrier includes indicators for advising the dentist as to how many times each bur in the carrier has been used. By tracking use on a bur by bur basis, premature disposal of used burs as well as the incidence of bur changes in the midst of procedures will be minimized while helping to prevent the negative consequences of overusing burs (i.e. intra-oral separation, excessive heat generation). The system also includes a used bur sterilization container, which mates with the carrier but can be separated from the carrier and placed in an autoclave for sterilization. This permits burs from the carrier to be kept separate from other burs during the sterilization process, which simplifies sorting and restocking, as well as permitting tracking of individual bur use. The system ensures hands-free sterilization, which further helps to prevent accidental exposure to the contaminated burs by the dental staff. This system also enables efficient inventory control of all burs purchased by the a practice by sorting them into easy to access restock and replace containers in each dental operatory.

27 Claims, 6 Drawing Sheets

| PROCEDURE | COLOR CODING |
|---|---|
| AMALGAM | GRAY |
| COMPOSITE | TAN |
| CROWN AND BRIDGE | YELLOW |
| VENEER | GREEN |
| ENDODONTIC ACCESS | PINK |
| BUILD-UP | BLUE |
| REMOVABLE PROSTHODONTICS | RED |
| ENDODONTICS | PURPLE |
| EMERGENCY PROCEDURES | WHITE |

|   |   |   |   |
|---|---|---|---|
| AMALGAM – WORKSHEET ||||
|   |   |   |   |
|   |   |   |   |
|   |   |   |   |

FIG. 7a

|   |   |   |   |
|---|---|---|---|
| COMPOSITE – WORKSHEET ||||
|   |   |   |   |
|   |   |   |   |
|   |   |   |   |

FIG. 7b

|   |   |   |   |
|---|---|---|---|
| CROWN & BRIDGE – WORKSHEET ||||
|   |   |   |   |
|   |   |   |   |
|   |   |   |   |

FIG. 7c

SYSTEM AND PROCESS FOR MANAGING DENTAL BURS

BACKGROUND OF THE INVENTION

1. Field of the Invention

This invention relates to dentistry, and in particular to the use and management of both disposable and reusable dental burs, which are the rotary drill-like elements that are used by dentists to cut, grind and shape teeth and restorative materials.

2. Description of the Related Technology

Modern dental practices in the United States and other countries must be equipped to perform a number of different procedures, such as the necessary preparations for amalgam and composite fillings, veneer, crown and bridge preparation, post and core procedures, endodontics, emergency treatments and procedures that are attendant to removable prosthodontics.

Dental burs, which are defined herein to include burs, files such as those that are in endodontic work, polishing wheels, and the like are available in hundreds of different shapes, sizes, and grits. For example, burs can be flat, rounded or pointed at the ends, and can be shaped as cones, inverted cones, double inverted cones, flames, pears, wheels, cylinders or any of many other shapes. Endodontic files, which are also defined as burs for purposes of this document, tend to be long and thin, which is ideal for cleaning and preparing the root canal chamber during endodontic procedures.

Every dentist has his or her preferences as to which particular burs to use for a given procedure. Accordingly, prior to performing a procedure, the dentist or dental assistant must ensure that each bur that the dentist prefers for use in the procedure is sterile and readily available. In addition, preparation must be made for other procedures that may become necessary during treatment, and spare burs of each type must be available in the event that the dentist deems a bur to be too worn for continued use.

After a procedure is completed, the used burs are collected for sterilization in an autoclave, where they may be mixed with burs from other procedures that were performed on the same or other patients, and with burs that were used by other dentists. The sterilized burs are then manually separated, sorted and returned to the appropriate dentist or room for reuse. This can be a very time consuming task.

Each bur has a limited useful lifespan, the extent of which depends on the amount of use it is given, the nature and intensity of the use, and the number of times that it has been cycled through the autoclave. Typically, a dentist will have little or no indication that a bur is at the end of its useful life until the bur fails to perform to expectations during a procedure. To avoid an annoying and inefficient hiatus in the midst of a critical procedure, it is not unusual for a dentist to intentionally avoid a used bur in favor of a new bur, and sometimes discard the used bur prematurely. Similarly, in an attempt to perform a dental procedure, a dentist may be forced to change burs several times as he or she searches for a productive bur. Every time the dentist changes the bur, she or he loses time, loses focus, becomes frustrated and increases the chance of accidentally sticking his or herself with a contaminated bur.

Burs represent a significant expense to dental practices, and such inefficient management of used burs increases this expense unnecessarily. Unfortunately, however, it has been difficult to address this problem because there is no effective way to track the number of times each bur has been used in a procedure and/or cycled through the autoclave.

A need exists for a system and process for managing dental burs that permits more efficient use of staff time in a dental practice, that makes it possible to keep track of the amount of use to which individual burs have been subjected, and that provides a systematic and easy method to learn the process of storing, using, sterilizing, stocking and reordering dental burs.

SUMMARY OF THE INVENTION

Accordingly, it is an object of the invention to provide a system and process for managing dental burs that permits more efficient use of staff time in a dental practice and that makes it possible to keep track of the amount of use to which individual burs have been subjected so as to make it possible to fully utilize each bur to its full potential. Accordingly, the invention helps prevent the negative consequences of overusing burs (i.e. intra-oral separation, excessive heat generation, etc.). The invention also provides a systematic and easy method to learn the process of storing, using, sterilizing, stocking and reordering dental burs.

In order to achieve the above and other objects of the invention, a method of managing dental burs according to a first aspect of the invention includes steps of: (a) using a dental bur; (b) storing the used dental bur; and (c) providing an indication to a dental professional that is specific to the stored used dental bur that is indicative of the extent to which the stored dental bur has been used.

A method of managing dental burs according to a second aspect of the invention includes steps of: (a) providing a dental bur carrier that has been configured according to the preferences of a particular dental professional; (b) removing a dental bur from the dental bur carrier; (c) using the dental bur; (d) returning the used bur to the carrier; and (e) providing an indication on the carrier that is specific to the used dental bur that is indicative of the extent to which the used dental bur has been used.

According to a third aspect of the invention, a method of customizing a set of dental burs in accommodation with the preferences of an individual dental professional, includes steps of: (a) recording information on the dental professional's preferences for a particular procedure; (b) sending the information to a configuring facility; and (c) configuring a dental bur carrier that is in conformance with the recorded preferences.

According to a fourth aspect of the invention, a system for storing a plurality of dental burs includes a carrier having a plurality of sockets defined therein, each of said sockets being constructed and arranged to receive one end of a dental bur; and an indicator for providing an indication to a dental professional that is specific to the extent to which at least one dental bur that is positioned in at least one of the sockets has been used.

A system for managing dental burs in accommodation to the preferences of individual dental professional(s) includes, according to a fifth aspect of the invention, a carrier having a plurality of sockets defined therein, each of said sockets being constructed and arranged to receive one end of a dental bur; a template on the carrier to aid in the proper identification of individual burs and proper placement of the burs in the respective sockets; and indicia on the carrier that is indicative of specific dental professional(s) and procedure (s) for which the system is configured.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIGS. 7(a) through 7(c) depict worksheets that may be used in accordance with the preferred method of practicing the invention.

DETAILED DESCRIPTION OF THE PREFERRED EMBODIMENT(S)

Figure 1:
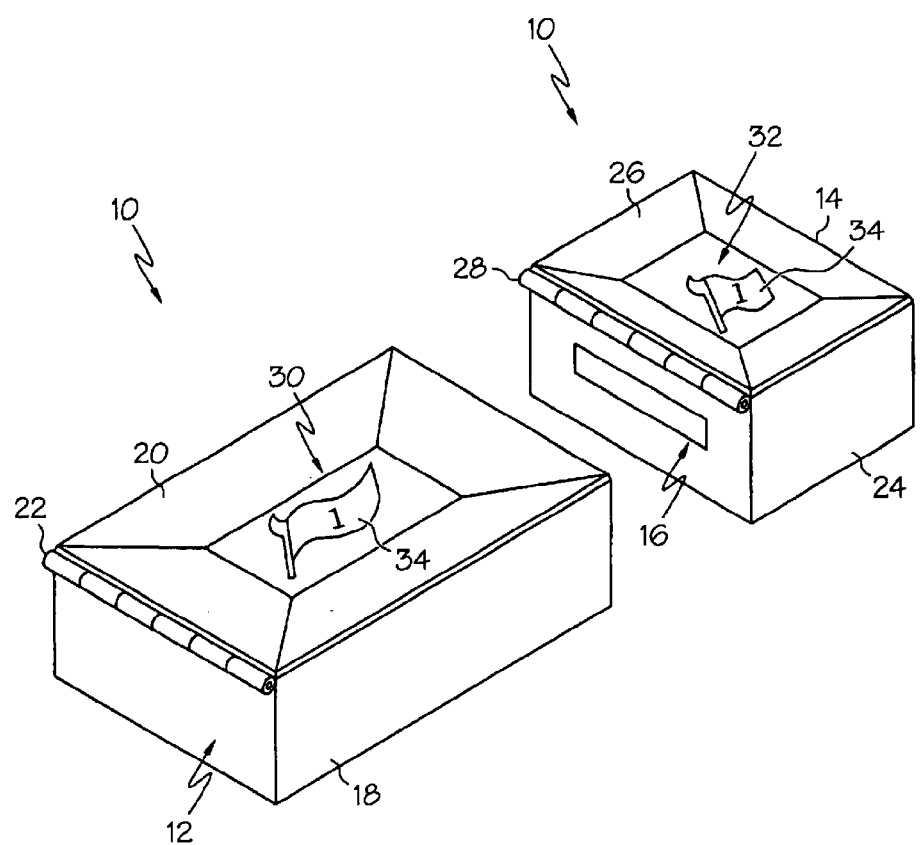
FIG. 1 is a perspective view of a bur management system that is constructed according to a preferred embodiment of the invention.
Figures 4, 5:
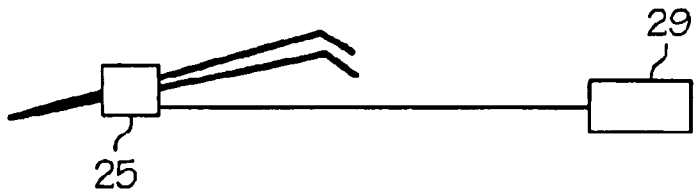
FIG. 4 is a table that depicts a color coding arrangement that is in accordance with the preferred embodiment of the invention.
FIG. 5 is a schematic view of a pair of college pliers that are constructed according to the preferred embodiment of the invention.

Referring now to the drawings, wherein like reference numerals designate corresponding structure throughout the views, and referring in particular to FIG. 1, a bur management system 10 that is constructed according to a preferred embodiment of the invention includes a carrier 12, a used bur container 14, and a releasable connector 16 that is provided for releasably securing the carrier 12 to the used bur container 14. As may be seen in FIG. 1, carrier 12 includes a body 18 and a lid 20, which is hinged with respect to the body 18 by means of a hinge 22. Similarly, the used bur container 14 has a body 24, a lid 26 and a hinge 28 for connecting the body 24 to the lid 26. The used bur container 14 may also have a clip or recess for receiving a pair of college pliers 25, which are illustrated in FIG. 5, for sterilization along with used burs that may be placed within the container 14.

As may be further seen in FIG. 1, indicia 30 is provided on the surface of the carrier 12, and preferably on the top surface of the lid 20, which is the surface that is most easily visible by the dentist or other dental professional. Similarly, the used bur container 14 has indicia 32 provided thereon on a top surface of lid 26. Both the carrier 12 and the used bur container 14 preferably have the same indicia printed thereon, which in the illustrated embodiment is a red flag 34 that has the numeral 1 printed thereon. The significance of this coding will be explained in greater detail below.

Figures 2, 3:
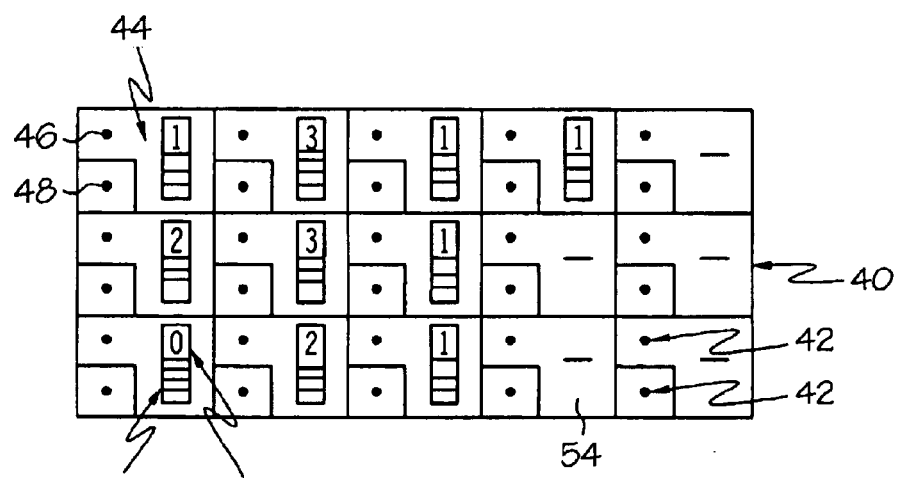
FIG. 2 is a plan view of one surface of the system that is shown in FIG. 1.
FIG. 3 is a plan view of another surface of the system that is shown in FIG. 1.

FIG. 2 depicts an inside surface 36 of the lid 20 of the carrier 12, which is provided with a template 38 to aid in the proper identification of individual burs and proper placement of the burs within the carrier 12. As may be seen in FIG. 2, the template 38 includes a profiled image of a number of different burs, each of which is positioned within a different cell 37 of the template 38. The template 38 is preferably a preprinted card that is insertable into the inside top lid 36 of the carrier 12, and that is protected against water damage and that may be wiped down periodically for cleaning.

Looking now to FIG. 3, it will be seen that the top surface 40 of the body 18 of carrier 12, which is visible when the lid 20 is opened, includes a corresponding number of cells 44, each of which includes a pair of sockets 42 that are constructed and arranged to receive one end of a dental bur. The sockets may be of diameters that are selected to match the assigned burs, or may be oversized in diameter with a magnetic centering system that keeps each bur centered in a socket, as is provided on certain commercially available bur block units. Specifically, each cell 44 is provided with a socket 46 that is designated for the storage of used burs, as well as a socket 48 that is designated for storage of new burs. Each cell 44 is also preferably provided with an indicator 50 for providing an indication to a dental professional that is specific to the extent to which at least one dental bur that is positioned in at least one of the sockets 46 has been used. In the illustrated embodiment, the indicator 50 is constructed as a manually adjustable numeric read out that is controlled by a thumb wheel 52 that is located within the corresponding cell 44. The thumb wheel 52 must have a manual override (i.e. push once to add one number to the recorded number of uses, hold for three seconds to reset uses to zero). This will allow the dentist to add uses to a bur that he or she feels worked "harder" during a particular procedure than normal. For example, a bur that is used for twenty seconds to remove a large amalgam filling will be more worn than a similar bur which was used for twenty seconds to cut a cavity preparation in natural tooth structure. Therefore, the dentist may want to ascribe two or three uses to the first bur while only attributing one use to the bur in the second example.

It will be apparent that while comparing the new or sterilized used burs with the template 38 that is shown in FIG. 2, a dental technician or assistant will be able to quickly and efficiently sort burs and position those burs in the appropriate cells 44 and sockets 46, 48 in the body 18 of the carrier 12.

FIG. 5 depicts a pair 25 of college pliers, which are customized according to the preferences of the dentist according to a specific procedure, and include indicia 27 thereon that is removably positioned within a holder 29. The indicia 27 of the college pliers 25 will correspond and match the indicia 30 of carrier 12 and the indicia 32 of the used bur block 14. The college pliers will be stored by some mechanism on either carrier 12 or the used bur block 14 so that they will be accessible to the dentist and the assistant. The dentist will remove the college pliers from its holder which may contaminate the handle of the college pliers but not the tip of the college pliers. The dentist will then use the sterilized tip to select a bur from the carrier 12 and return the college pliers to its holder without contaminating the other sterile burs contained in carrier 12 or the sterilized tip of the college pliers. At the completion of a dental procedure, the college pliers will be sterilized along with the contaminated burs located in the used bur block 14 so as to sterilize the contaminated college pliers handle, burs, and used bur block. When the used burs, the used bur block and the corresponding college pliers have completed the sterilization process they will be returned to the corresponding carrier 12 and the assistant will return the used burs to their correct socket 46 using the sterile college pliers while wearing clean gloves.

According to the preferred embodiment of the invention, the outer case 54 (or a portion thereof, such as the lid 20) of the carrier 12 and likewise that of the used bur container 14 as well as the indicia 27 on the college pliers 25 is preferably color coded to indicate the type of procedure for which the selection of burs that are contained within the carrier 12 are selected and customized. As is illustrated in the table that is shown in FIG. 4, a carrier 12 that is intended for use in an amalgam procedure is given a gray color coding, while a carrier for a composite procedure is given a tooth tone coloring. A carrier 12 for a crown or bridge procedure is color-coded yellow, while a carrier for a veneer procedure is color-coded green. Carriers 12 that are customized for endodontic access procedures are given a pink color coding, while a carrier 12 that is customized for a build up procedure is color-coded blue. Likewise, a carrier may be provided for removable prosthodontics that is color coded, for example, red, while others may be provided for endodontics, and emergency procedures that are color coded, again for example, purple and white, respectively. The specific colors selected for the respective procedures are arbitrary, and this aspect of the invention should not be considered so limited.

Figure 6:
FIG. 6 is a top plan view of another component of the system that is shown in FIG. 1.

As is illustrated in FIG. 6, another aspect of the invention is the provision within the bur management system 10 of a master re-stocking and inventory controlling container 56 that includes a number of compartments, and further includes a stocking template on the top surface thereof to indicate a particular dentist's preferences insofar as bur selection is concerned for a number of different commonly performed procedures.

Essentially this container will include a base that will contain compartments which will separate and store the new burs as they are packaged from the manufacturer in an orderly manner starting from the lowest number bur (i.e. ¼ round) to the highest number bur (i.e. 897K-016). This numerical ordering will allow for easy location and retrieval of the new burs. The lid will display a customized re-stocking template of all the burs used by the dentist and which procedure set ups should include which burs.

In order to create and fill the master container 56, the dentist will first complete the worksheets described below with reference to FIGS. 7(a), 7(b), and 7(c), for every procedure (FIG. 4) the dentist performs in the dental practice. For each procedure, the dentist will list which burs he or she uses and in which order he or she most commonly uses them from the start to the finish. Once these worksheets are completed, the bur selections will be configured by this invention to produce all the necessary components including the restocking template for the master container 56, the templates 38 for each procedure, and the corresponding indicia 30, 32, and 27 so that all the components match. The master template 56 will reflect the required bur inventory for the dentist. The dentist will now order the correct number of burs from the bur manufacturer in the most efficient manner. Most manufacturers offer discounts when ordering in bulk, therefore this system will help the dentist to reduce his or her overall cost per bur while allowing the dentist to store the burs in an easily accessible system.

The assistant will then fill the master container base 56 with the new burs from the bulk ordering. The dentist will have one master container 56 in each operatory from which the burs of carrier 12 for each procedure (FIG. 4) in that room will be restocked. The dentist or assistant will then set up each carrier 12 with the necessary burs as delineated by each template 38 and the matching restocking template 56. Upon set-up completion the assistant will fill the master carrier again so as to completely stock each room.

During the course of dental procedures, the dentist will chose the used bur from socket 46 with the sterile college pliers 25 and will use it until he or she deems that the bur is too dull to continue. The dentist will then discard the used bur and will select the matching new bur from socket 48. After the completion of the procedure the dental assistant will access the master carrier for that room, select the corresponding bur and restock the new bur into socket 48 of the carrier 12.

Periodically, the assistant will take inventory of the burs in the master carrier and record the exact bur name, number, and description as delineated on the master restocking template of the burs which need to be ordered; thereby easily creating a bur order form. This quick access to, retrieval and inventory of the burs in the master carrier will allow the dental practice to ensure that it has the necessary burs to perform the required dental procedures.

As may be seen in FIG. 6, the re-stocking container 56 makes it easy to stock and keep track of bur supplies for a particular dentist (and/or room or practice) for such procedures including but not limited to amalgam, composite procedures, crown or bridge procedures, veneer procedures, endodontic access procedures and build up procedures. Re-stocking container 56 is also color coded in the same mode as the carrier 12 used bur container 14 and the college pliers 25, in the manner that is described above. The color coding can alternatively represent different physical locations, such as rooms, within a practice, or groups of dentists, or of rooms, as may be desired within the practice. Another important aspect of the invention is the procedures that enable the dental supplier, dental office or manufacturer to customize the carriers 12, college pliers 25, the re-stocking containers 56 and/or the configuration of the overall system to the preferences of individual dentists as described above. Many dental offices are equipped with personal computers, and some utilize technology that permits tooth imaging data, patient records and the like to be stored and viewed with the aid of those computers. Other dental offices, however, are not so equipped, and still rely on manual storage and retrieval for X-rays, patient records, and other data. Therefore this invention will allow the dentist to customize their system based on their needs and access to the necessary technology. For example the high-tech offices may want to customize their system in their office while others may want to allow the manufacturer to send them the completed system.

Referring now to FIGS. 7(a), 7(b) and 7(c), work sheets are depicted that will permit a dentist or other dental professional to record his or her preferences as to the number and identity of dental burs that are preferred for a particular procedure. For example, FIG. 7(a) is a worksheet that permits a dentist or other dental professional to specify the selection of and order of use of burs that are preferred for an amalgam procedure, while FIGS. 7(b) and 7(c) depict worksheets for composite procedures and crown and bridge procedures, respectively. These worksheets are provided as examples only, and other worksheets are expected to be provided for the other procedures that are listed above. The worksheets may be provided as printed forms for dental offices that do not utilize computer technology, and the completed forms may be mailed or transmitted via facsimile to a manufacturer or dental supplier, which in turn will customize a carrier or set of carriers and a re-stocking container for the preferences of that individual dentist.

Alternatively, a worksheet may be inserted into a carrier 12 as a substitute from the template 38 described above, and likewise into the corresponding indicia 32 of the used bur container 14 and the indicia 27 of the corresponding college pliers 25 as templates as described above with reference to FIG. 2 so as to enable the dental office to customize a carrier itself for an individual dental professional. This option may also be used as a temporary measure while a permanent carrier 12 is being manufactured to order.

For the growing number of offices that utilize computers, and particularly that are equipped with electronic modems, software may be provided that will permit a dentist or other dental professional to fill out these worksheets electronically, with the resulting information being transmitted to the dental supplier or manufacturer via the modem. As another alternative, the dental supplier or manufacturer may provide an Internet site that includes similar worksheets for a dentist or other dental professional to fill out.

Figure 8:
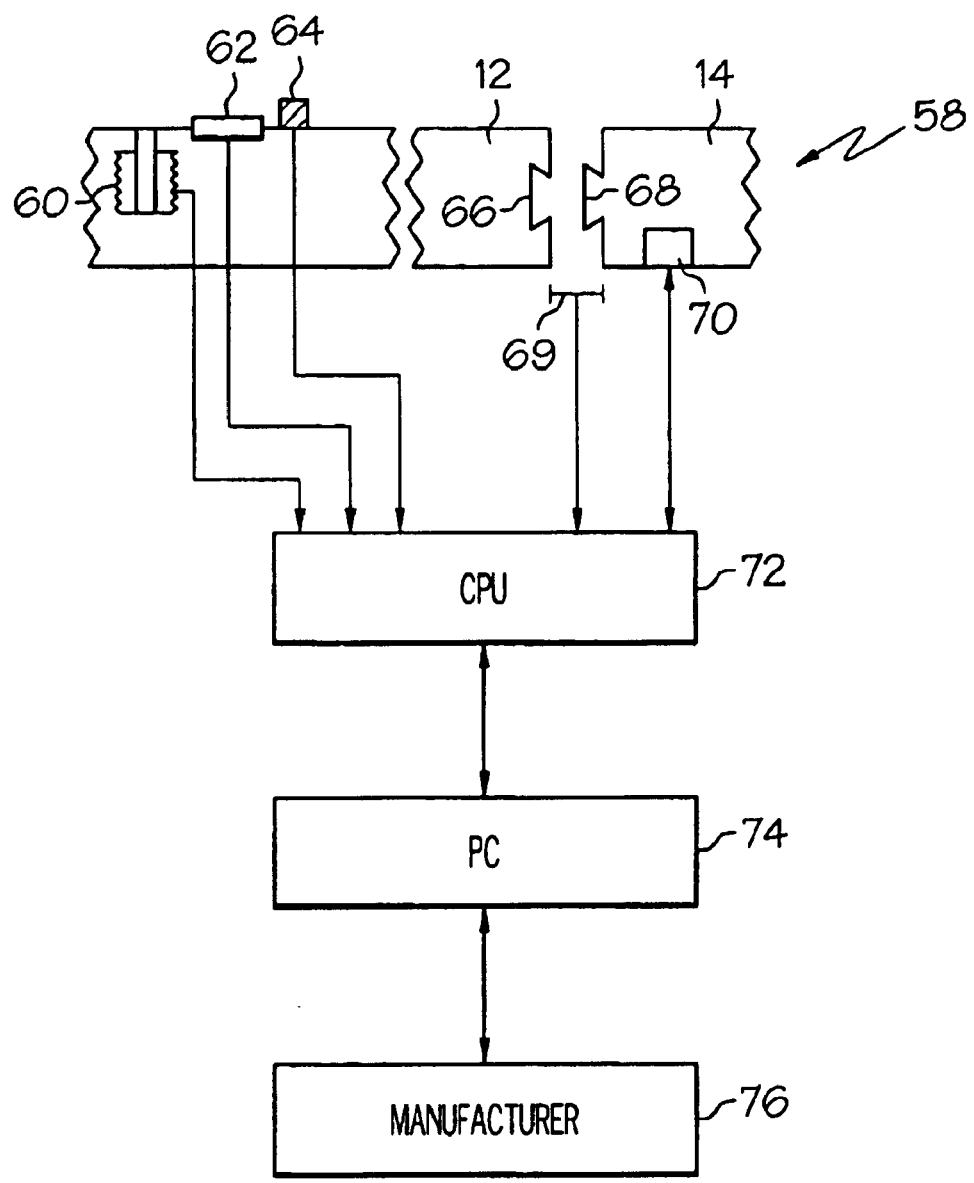
FIG. 8 is a schematic diagram depicting a system that is constructed according to a second embodiment of the invention.

FIG. 8 depicts a bur management system 58 that is constructed according to a second embodiment of the invention. In this embodiment, a carrier 12, which except as described herein is identical to that described in the previous embodiment, is provided with a sensor 60 that is capable of detecting whether one end of a dental bur is present within a particular socket. Preferably, such sensors 60 are provided in every socket that is defined in the carrier 12. Sensors 60 are preferably inductive in nature, so as to require little or no external power to be able to perform the sensing function. In addition, each cell in the carrier 12 is preferably provided with an electronic display 62, which may be a conventional liquid crystal display or light emitting diode display that will be capable of giving a numerical readout, and is similar in its function to the indicator 50 that is described above with reference to FIG. 3. Each cell in the carrier 12 is further provided with a reset button 64, the purposes of which will be described below.

As may be seen in FIG. 8, the carrier 12 is connectable to the used bur container 14 by a releasable connector 16 that includes a tongue 68 on the used bur container 14 and a mating groove 66 that is defined in the carrier 12. An electronic sensor 69, which is preferably constructed as a simple switch that is closed when contact is made between the tongue 68 and the groove 66, is provided for indicating when the carrier 12 is coupled to the used bur container 14. In addition, an electronically resettable thermally actuated switch 70 is provided within the used bur container 14, the function of which will be described below.

As is shown schematically in FIG. 8, a CPU 72 is included in the bur management system 58 which is configured to receive information from the inductive sensors 60, the reset buttons 64, the sensor 69 for determining when the carrier 12 is coupled to the container 14, and for receiving information from the thermal switch 70. Moreover, the CPU 72 is configured to provide information to the electronic displays 62 and to reset the thermal switch 70, for the purposes that will be described below. CPU 72 is also preferably connected in two-way communication with a personal computer 74, which in turn is capable of electronic communication, such as by a dedicated connection or a modem connection via direct dial up access or internet access to a dental supplier or manufacturer 76. Alternatively, the CPU could be eliminated, and its functions could be assimilated into the processor of the personal computer 74. Structurally, the CPU 72 could be within a stand-alone unit, or it could be integrated into the carrier 12.

In the preferred mode of operation, the CPU will record the number of uses for a particular dental bur that is stored in each cell of the carrier 12. When a new dental bur is removed from the socket 48 that is provided for unused burs with a cell, this is sensed by the sensor 60 that is provided in that socket 48, and this information is transmitted to the CPU 72, which will clear the register and indicate on the electronic display a 62 that this particular bur that is in use has no previous use cycles. After use, the dentist or other dental professionals will place the used bur, as well as other used burs from the procedure that has been performed, within the used bur container 14. At the conclusion of the procedure, or at the end of the day, whichever is more convenient, the used bur container 14 will be separated from the carrier 12, and this event will be recorded by the CPU 72 by information received from the sensor 69. The lid of the used bur container 14 is then closed, thereby initiating the hands-free sterilization process, and is taken to the autoclave so that the used burs stored therein are sterilized. The autoclave procedure will close the thermally actuated switch 70 provided that the correct sterilization environment has been achieved. After autoclaving, the used bur container 14 will be the attached to the carrier 12. It is essential that the used bur container 14 is paired and mated with the same carrier 12 that it was originally attached to. This is accomplished by matching the indicia 30, 32 that is provided on the carrier 12 and the used bur container 14. It is expected that an individual dentist will have more than one carrier 12 for each procedure, as he or she will be expected to perform several procedures of a certain type, e.g. amalgams, in a given day. In order to accurately track bur usage, it is important that a used bur container from one amalgam procedure, for example, not be mated to a amalgam carrier that was not used in that same procedure. To prevent such mismatching, the different amalgam carriers for a particular dentist (and their corresponding used bur containers) are preferably numbered. For example, the indicia 30, 32 on the carrier 12 and container 14 shown in FIG. 1 is styled as a red flag including the numeral "1," and the carrier 12 and the container 14 themselves are color coded gray. The gray color coding indicates that the carrier 12 and container 14 are set up for an amalgam procedure, as described above. The red flag symbolizes a particular dentist (if the dentist practices in an assigned room, the room may also be designated with that color coding), while the numeral "1" indicates that this is the first amalgam set for that particular dentist in that particular room.

Alternatively, the carrier 12 and the container 14 could be electronically paired so that they recognize each other and will not operate with any other unit, and so that a warning is given when a coupling to an inappropriate unit is attempted.

When the carrier 12 and the used bur container 14 are attached, this information is transmitted to the CPU 72 by the sensor 69, and the thermal switch 70 will indicate to the CPU 72 that the used burs have in fact undergone autoclaving. At this point, the dental assistant or technician will open the lid of the container 14 and remove the sterilized used burs one by one with the concomitantly sterilized and matching college pliers. Each bur is compared to the template 38 that is illustrated in FIG. 2, and is then placed in the appropriate used bur socket 46 in the correct cell 44 of the carrier 12. As it is placed in a socket, this information will be transmitted to the CPU 72 by the corresponding sensor 60. The CPU 72 will then cause the electronic display 62 to increment by one use, thus providing an accurate indication to the dental professional as to the degree of use of that particular used bur. At about this point in time, the CPU 72 will then electronically reset the thermally actuated switch 70.

At any point during a procedure, the dentist may manually adjust the system through use of the reset button 64. The reset button has dual functionality: push once to add one use to the corresponding bur allowing the dentist to customize the indicated number of uses or push and hold for three seconds to reset the indicated number of uses to zero.

Accordingly, the invention provides a system and process for managing dental burs that permits more efficient use of staff time in a dental practice, and that makes it possible to keep track of the amount of use to which individual burs have been subjected.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, color-coding scheme and arrangement of parts within the principles of the invention to the full extent indicated by the broad general meaning of the terms in which the appended claims are expressed.

What is claimed is:

1. A method of managing dental burs, comprising steps of:
   (a) using a dental bur;
   (b) storing the used dental bur in a storage carrier; and
   (c) providing an indication on the storage carrier to a dental professional that is specific to the stored used dental bur that is indicative of the extent to which the stored dental bur has been used.

2. A method according to claim 1, further comprising a step of sterilizing the dental bur prior to step (c).

3. A method according to claim 1, wherein said storage carrier is configured to store all burs that may be necessary for a particular procedure.

4. A method according to claim 3, wherein the storage carrier is further configured to store a collection of dental burs that is in conformance with the preferences of an individual dentist.

5. A method according to claim 1, wherein said storage carrier is configured to store a collection of dental burs that is in conformance with the preferences of an individual dentist.

6. A method according to claim 1, wherein step (c) is performed by providing a visual indication of the number of times that the stored used dental bur has been used.

7. A method according to claim 6, further comprising a step of manually setting the visual indication at some point after step (a).

8. A method according to claim 1, further comprising a step of storing a new dental bur that is of the same type as the stored used dental bur in a common storage carrier as the used dental bur.

9. A method of managing dental burs, comprising steps of:
   (a) providing a dental bur carrier that has been configured according to the preferences of a particular dental professional;
   (b) removing a dental bur from the dental bur carrier;
   (c) using the dental bur;
   (d) returning the used bur to the carrier; and
   (e) providing an indication on the carrier that is specific to the used dental bur that is indicative of the extent to which the used dental bur has been used.

10. A method according to claim 9, further comprising a step, performed after step (c), of sterilizing the used dental bur.

11. A method according to claim 10, wherein said step of sterilizing comprises steps of placing the used dental bur into an autoclavable container that is identifiable as being specific to the carrier.

12. A method according to claim 11, wherein the autoclavable container is constructed and arranged to be releasably secured to the carrier, and wherein the step of sterilizing further comprises detaching the autoclavable container from the carrier.

13. A method according to claim 11, wherein the autoclavable container is constructed and arranged to allow for hands-free sterilization processing of contaminated dental burs after completion of the dental procedure.

14. A method according to claim 9, wherein the carrier has identification means thereon for permitting recognition of a specific bur, and wherein step (d) comprises using the identification means to identify the bur and placing the bur in a predetermined location in the carrier.

15. A method according to claim 9, wherein step (a) comprises steps of collecting information on the preferences of a particular dental professional, and customizing the carrier for those preferences.

16. A method according to claim 15, wherein said step of collecting information comprises transmitting the preferences electronically.

17. A system for storing a plurality of dental burs, comprising:
   a carrier having a plurality of sockets defined therein, each of said sockets being constructed and arranged to receive one end of a dental bur; and
   indicator means on said carrier for providing an indication to a dental professional that is specific to the extent to which at least one dental bur that is positioned in at least one of said sockets has been used.

18. A system according to claim 17, wherein said indicator means comprises a plurality of indicators, each of said indicators being specific to one stored dental bur.

19. A system according to claim 17, wherein said indicator means comprises means for visually indicating the number of times a particular dental bur has been used.

20. A system according to claim 19, wherein said indicator means comprises a manually adjustable numeric readout.

21. A system according to claim 19, wherein said indicator means comprises an electronic numeric readout and means for automatically adjusting the readout after a bur has been removed and replaced.

22. A system according to claim 17, wherein said carrier has a first plurality of sockets that are designated for receiving used dental burs, and a second plurality of sockets for receiving new dental burs, whereby a new dental bur will be available if it is deemed advisable to use a new bur in favor of a used bur.

23. A system according to claim 17, further comprising template means on said carrier to aid in the proper identification of individual burs and proper placement of the burs in the respective sockets.

24. A system according to claim 23, wherein said template means is customized to be in accommodation to the preferences of a specific dental professional.

25. A system according to claim 17, further comprising an autoclavable used bur container for receiving used burs during sterilization, said used bur container being identifiable as corresponding to a specific carrier.

26. A system according to claim 25, further comprising means for releasably attaching said used bur container to said carrier.

27. A system according to claim 17, further comprising an autoclavable college plier that is configured to permit sterile removal of burs from the carrier without contaminating burs that are not used during a specific procedure, said burs having indicia provided thereon that is indicative as being identifiable to a specific carrier.

* * * * *